US009863883B2

(12) United States Patent
Shibayama et al.

(10) Patent No.: US 9,863,883 B2
(45) Date of Patent: *Jan. 9, 2018

(54) SURFACE-ENHANCED RAMAN SCATTERING ELEMENT

(71) Applicant: HAMAMATSU PHOTONICS K.K., Hamamatsu-shi, Shizuoka (JP)

(72) Inventors: Katsumi Shibayama, Hamamatsu (JP); Masashi Ito, Hamamatsu (JP); Takafumi Yokino, Hamamatsu (JP); Masaki Hirose, Hamamatsu (JP); Anna Yoshida, Hamamatsu (JP); Kazuto Ofuji, Hamamatsu (JP); Yoshihiro Maruyama, Hamamatsu (JP); Takashi Kasahara, Hamamatsu (JP); Toshimitsu Kawai, Hamamatsu (JP); Toru Hirohata, Hamamatsu (JP); Hiroki Kamei, Hamamatsu (JP); Hiroki Oyama, Hamamatsu (JP)

(73) Assignee: HAMAMATSU PHOTONICS K.K., Hamamatsu-shi, Shizuoka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/420,502

(22) PCT Filed: Aug. 9, 2013

(86) PCT No.: PCT/JP2013/071704
§ 371 (c)(1),
(2) Date: Feb. 9, 2015

(87) PCT Pub. No.: WO2014/025035
PCT Pub. Date: Feb. 13, 2014

(65) Prior Publication Data
US 2015/0212003 A1  Jul. 30, 2015

(30) Foreign Application Priority Data

Aug. 10, 2012 (JP) .................................. 2012-178763
Aug. 10, 2012 (JP) .................................. 2012-178765

(Continued)

(51) Int. Cl.
*G01N 21/65* (2006.01)
*G01N 21/03* (2006.01)
*B82Y 40/00* (2011.01)

(52) U.S. Cl.
CPC ........... *G01N 21/658* (2013.01); *G01N 21/03* (2013.01); *B82Y 40/00* (2013.01); *G01N 2201/068* (2013.01)

(58) Field of Classification Search
CPC .................................................. G01N 21/658
See application file for complete search history.

(56) References Cited

U.S. PATENT DOCUMENTS 4,589,551 A  5/1986  Hellon
5,090,568 A  2/1992  Tse
(Continued)

FOREIGN PATENT DOCUMENTS

CN  1563989  1/2005
CN  1957245  5/2007
(Continued)

OTHER PUBLICATIONS

U.S. Office Action dated Dec. 10, 2015 that issued in U.S. Appl. No. 14/420,404 including Double Patenting Rejections on pp. 12-15.
(Continued)

*Primary Examiner* — Shawn Decenzo
(74) *Attorney, Agent, or Firm* — Drinker Biddle & Reath LLP

(57) ABSTRACT

A SERS element comprises a substrate having a front face; a fine structure part formed on the front face and having a (Continued)

plurality of pillars; and a conductor layer formed on the fine structure part and constituting an optical function part for generating surface-enhanced Raman scattering. The conductor layer has a base part formed along the front face and a plurality of protrusions protruding from the base part at respective positions corresponding to the pillars. The base part is formed with a plurality of grooves surrounding the respective pillars when seen in the projecting direction of the pillars, while an end part of the protrusion is located within the groove corresponding thereto.

8 Claims, 14 Drawing Sheets

(30) Foreign Application Priority Data

| Aug. 10, 2012 | (JP) | 2012-178766 |
|---|---|---|
| Aug. 10, 2012 | (JP) | 2012-178767 |
| Aug. 10, 2012 | (JP) | 2012-178768 |
| Aug. 10, 2012 | (JP) | 2012-178771 |
| Aug. 10, 2012 | (JP) | 2012-178773 |
| Aug. 10, 2012 | (JP) | 2012-178778 |
| Aug. 10, 2012 | (JP) | 2012-178976 |
| Mar. 29, 2013 | (JP) | 2013-073308 |
| Mar. 29, 2013 | (JP) | 2013-073312 |
| Mar. 29, 2013 | (JP) | 2013-073315 |
| Mar. 29, 2013 | (JP) | 2013-073444 |
| Jul. 5, 2013 | (JP) | 2013-142164 |

(56) References Cited

U.S. PATENT DOCUMENTS

| 5,655,661 | A | 8/1997 | Rigby |
|---|---|---|---|
| 5,772,905 | A | 6/1998 | Chou |
| 6,582,996 | B1 | 6/2003 | Hara et al. |
| 6,614,523 | B1 | 9/2003 | Boss et al. |
| 6,967,717 | B1 | 11/2005 | Boss et al. |
| 6,970,239 | B2 | 11/2005 | Chan et al. |
| 7,148,964 | B2 | 12/2006 | Cunningham et al. |
| 7,236,242 | B2 | 6/2007 | Kamins et al. |
| 7,428,046 | B2 | 9/2008 | Wang et al. |
| 7,460,224 | B2 | 12/2008 | Wang et al. |
| 7,483,130 | B2 | 1/2009 | Baumberg et al. |
| 7,545,490 | B1 | 6/2009 | Pendell-Jones |
| 7,876,425 | B2 | 1/2011 | Sardashti et al. |
| 8,416,406 | B2 | 4/2013 | Stuke et al. |
| 9,127,984 | B2 | 9/2015 | Tseng et al. |
| 9,267,894 | B2 | 2/2016 | Ito et al. |
| 2003/0059820 | A1 | 3/2003 | Vo-Dinh |
| 2003/0157732 | A1 | 8/2003 | Baker et al. |
| 2003/0235520 | A1 | 12/2003 | Shea et al. |
| 2004/0023046 | A1 | 2/2004 | Schlottig et al. |
| 2005/0224253 | A1 | 10/2005 | Aoki et al. |
| 2006/0034729 | A1 | 2/2006 | Poponin |
| 2006/0061762 | A1 | 3/2006 | Dwight et al. |
| 2006/0119250 | A1 | 6/2006 | Suehiro et al. |
| 2006/0146323 | A1 | 7/2006 | Bratkovski et al. |
| 2006/0164637 | A1 | 7/2006 | Wang |
| 2007/0015288 | A1 | 1/2007 | Hulteen et al. |
| 2007/0140900 | A1 | 6/2007 | Wang et al. |
| 2007/0145249 | A1 | 6/2007 | Kiesel et al. |
| 2007/0153267 | A1 | 7/2007 | Wang et al. |
| 2007/0254377 | A1 | 11/2007 | Li et al. |
| 2008/0073206 | A1 | 3/2008 | Nogawa |
| 2008/0094621 | A1 | 4/2008 | Li et al. |
| 2008/0142822 | A1 | 6/2008 | Kim et al. |
| 2008/0174775 | A1 | 7/2008 | Moskovits et al. |
| 2008/0218761 | A1 | 9/2008 | Nishikawa et al. |
| 2008/0297802 | A1 | 12/2008 | Ogawa et al. |
| 2009/0108181 | A1 | 4/2009 | Ishihara et al. |
| 2009/0137411 | A1 | 5/2009 | Sun et al. |
| 2009/0231586 | A1 | 9/2009 | Murakami et al. |
| 2010/0009456 | A1 | 1/2010 | Prins et al. |
| 2010/0019355 | A1 | 1/2010 | Kamins et al. |
| 2010/0078860 | A1 | 4/2010 | Yoneda et al. |
| 2010/0085566 | A1 | 4/2010 | Cunningham |
| 2010/0195106 | A1 | 8/2010 | Ogawa |
| 2010/0240144 | A1 | 9/2010 | Gilbert |
| 2010/0296086 | A1 | 11/2010 | Wang et al. |
| 2010/0321684 | A1 | 12/2010 | Bratkovski et al. |
| 2011/0027901 | A1 | 2/2011 | Gaster et al. |
| 2011/0096157 | A1 | 4/2011 | Fine et al. |
| 2011/0116089 | A1* | 5/2011 | Schmidt ............... G01N 21/658 356/301 |
| 2011/0166045 | A1 | 7/2011 | Dhawan et al. |
| 2011/0194116 | A1 | 8/2011 | Horiuchi et al. |
| 2011/0267607 | A1 | 11/2011 | Hu et al. |
| 2011/0267608 | A1 | 11/2011 | Ou et al. |
| 2011/0300691 | A1 | 12/2011 | Sakamoto et al. |
| 2011/0317160 | A1 | 12/2011 | Li et al. |
| 2012/0081703 | A1 | 4/2012 | Moskovits et al. |
| 2012/0086021 | A1 | 4/2012 | Wang |
| 2012/0105841 | A1 | 5/2012 | Hu et al. |
| 2012/0162640 | A1 | 6/2012 | Sakagami |
| 2012/0170033 | A1 | 7/2012 | Zhu et al. |
| 2012/0182548 | A1 | 7/2012 | Harb et al. |
| 2012/0265038 | A1 | 10/2012 | Kawamura et al. |
| 2013/0142987 | A1 | 6/2013 | Wardle et al. |
| 2013/0176562 | A1 | 7/2013 | Shioi et al. |
| 2013/0252275 | A1 | 9/2013 | Tokonami et al. |
| 2014/0028995 | A1 | 1/2014 | Bratkovski et al. |
| 2014/0043605 | A1* | 2/2014 | Tseng .................. G01J 3/44 356/301 |
| 2014/0045209 | A1 | 2/2014 | Chou et al. |
| 2014/0154668 | A1 | 6/2014 | Chou et al. |
| 2014/0218727 | A1 | 8/2014 | Li et al. |
| 2014/0347661 | A1 | 11/2014 | Kim et al. |
| 2015/0204792 | A1 | 7/2015 | Shibayama et al. |
| 2015/0211999 | A1 | 7/2015 | Maruyama et al. |
| 2015/0212000 | A1 | 7/2015 | Maruyama et al. |
| 2015/0212002 | A1 | 7/2015 | Ito et al. |
| 2015/0212003 | A1 | 7/2015 | Shibayama et al. |
| 2015/0219562 | A1 | 8/2015 | Shibayama et al. |
| 2015/0233832 | A1 | 8/2015 | Maruyama et al. |
| 2015/0233833 | A1 | 8/2015 | Shibayama et al. |
| 2015/0338346 | A1 | 11/2015 | Chou et al. |
| 2016/0061736 | A1 | 3/2016 | Ito et al. |
| 2016/0146736 | A1 | 5/2016 | Chen et al. |

FOREIGN PATENT DOCUMENTS

| CN | 101024483 | 8/2007 |
|---|---|---|
| CN | 101057132 | 10/2007 |
| CN | 101223435 | 7/2008 |
| CN | 101281133 | 10/2008 |
| CN | 101400976 | 4/2009 |
| CN | 101408513 | 4/2009 |
| CN | 101460830 | 6/2009 |
| CN | 101490535 | 7/2009 |
| CN | 101523212 | 9/2009 |
| CN | 101529229 | 9/2009 |
| CN | 101566571 | 10/2009 |
| CN | 101629906 | 1/2010 |
| CN | 101672784 | 3/2010 |
| CN | 101680900 | 3/2010 |
| CN | 101910829 | 12/2010 |
| CN | 101936906 | 1/2011 |
| CN | 102016585 | 4/2011 |
| CN | 102072878 | 5/2011 |
| CN | 102103086 | 6/2011 |
| CN | 102169086 | 8/2011 |
| CN | 102169088 | 8/2011 |
| CN | 102282094 | 12/2011 |
| CN | 102307699 | 1/2012 |
| CN | 102330080 | 1/2012 |
| CN | 102348966 | 2/2012 |
| CN | 102472665 | 5/2012 |
| CN | 102483354 | 5/2012 |
| CN | 102483866 | 5/2012 |
| CN | 102590088 | 7/2012 |

(56) References Cited

FOREIGN PATENT DOCUMENTS

| | | |
|---|---|---|
| CN | 102713720 | 10/2012 |
| CN | 103930780 | 7/2014 |
| CN | 104011520 | 8/2014 |
| EP | 1374989 | 1/2004 |
| EP | 2101166 | 9/2009 |
| EP | 2278301 | 1/2011 |
| EP | 2352010 | 8/2011 |
| EP | 2386847 | 11/2011 |
| EP | 2469598 | 6/2012 |
| GB | 2419940 | 5/2006 |
| GB | 2436719 | 10/2007 |
| JP | S56-142454 | 10/1981 |
| JP | H05-044867 U | 6/1993 |
| JP | H07-260646 A | 10/1995 |
| JP | 2003-026232 A | 1/2003 |
| JP | 2003-240705 | 8/2003 |
| JP | 2005-337771 A | 12/2005 |
| JP | 2006-208271 | 8/2006 |
| JP | 2006-250924 | 9/2006 |
| JP | 2007-530925 A | 11/2007 |
| JP | 2007-538264 A | 12/2007 |
| JP | 2008-064574 | 3/2008 |
| JP | 2008-128786 | 6/2008 |
| JP | 2008-519254 A | 6/2008 |
| JP | 2008-196992 A | 8/2008 |
| JP | 2008-268059 A | 11/2008 |
| JP | 101319994 | 12/2008 |
| JP | 2009-025316 A | 2/2009 |
| JP | 2009-047623 A | 3/2009 |
| JP | 2009-103643 A | 5/2009 |
| JP | 2009-222507 A | 10/2009 |
| JP | 2009-236830 A | 10/2009 |
| JP | 2009-544967 A | 12/2009 |
| JP | 2010-506191 A | 2/2010 |
| JP | 2010-230352 | 10/2010 |
| JP | 2011-021085 | 2/2011 |
| JP | 2011-033518 A | 2/2011 |
| JP | 2011-506916 A | 3/2011 |
| JP | 2011-075348 A | 4/2011 |
| JP | 2011-107032 A | 6/2011 |
| JP | 2011-141264 | 7/2011 |
| JP | 2011-141265 A | 7/2011 |
| JP | 2011-201769 | 10/2011 |
| JP | 2011-215021 A | 10/2011 |
| JP | 2012-063293 | 3/2012 |
| JP | 2012-508881 | 4/2012 |
| JP | 2012-233707 A | 11/2012 |
| JP | 2013-173444 | 9/2013 |
| JP | 2014-037969 | 2/2014 |
| JP | 2014-196974 | 10/2014 |
| JP | 2014-196981 | 10/2014 |
| JP | 5779963 | 9/2015 |
| TW | 200728706 | 8/2007 |
| TW | 200932913 | 8/2009 |
| TW | 201111771 | 4/2011 |
| TW | 201410591 | 3/2014 |
| WO | WO 2002-004951 | 1/2002 |
| WO | WO 2006/138442 | 12/2006 |
| WO | WO-2007/149120 A2 | 12/2007 |
| WO | WO 2008/030666 | 3/2008 |
| WO | WO 2010/033267 | 3/2010 |
| WO | WO-2010/050203 A1 | 5/2010 |
| WO | WO-2010/090111 A1 | 8/2010 |
| WO | WO 2010/104520 | 9/2010 |
| WO | WO-2011/021085 A2 | 2/2011 |
| WO | WO 2011/022093 | 2/2011 |
| WO | WO-2011/040501 A1 | 4/2011 |
| WO | WO 2011/047199 | 4/2011 |
| WO | WO 2011/121857 | 10/2011 |
| WO | WO-2012/024006 A2 | 2/2012 |
| WO | WO 2012/077756 | 6/2012 |
| WO | WO 2013/015810 | 1/2013 |
| WO | WO 2013/058739 | 4/2013 |
| WO | WO 2013/062540 | 5/2013 |
| WO | WO-2014/025033 A1 | 2/2014 |
| WO | WO-2014/025034 A1 | 2/2014 |
| WO | WO 2014/156329 | 10/2014 |

OTHER PUBLICATIONS

U.S. Office Action dated Dec. 14, 2015 that issued in U.S. Appl. No. 14/420,422 including Double Patenting Rejections on pp. 8-11.

"Q-SERS™ G1 Substrate," Opto Science, Inc. (retrieved on-line on Jul. 5, 2013).

Masahiro Yanagisawa, "Detection of Trace Organic Gas Using Molecular Sensor with Plasmon Antenna," Green Technology, Vo. 22, No. 6, Jun. 10, 2012, pp. 42-47, including at least partial English-language translation.

English-language translation of International Preliminary Report on Patentability (IPRP) dated Oct. 8, 2015 that issued in WO Patent Application No. PCT/JP2014/052926.

English-language translation of International Preliminary Report on Patentability (IPRP) dated Oct. 8, 2015 that issued in WO Patent Application No. PCT/JP2014/052927.

English-language translation of International Preliminary Report on Patentability (IPRP) dated Oct. 8, 2015 that issued in WO Patent Application No. PCT/JP2014/052928.

U.S. Office Action dated Oct. 19, 2015 that issued in U.S. Appl. No. 14/420,483 including Double Patenting Rejections on pp. 13-15.

Wei Fen Jiang et al., "Improved surface-enhanced Raman scattering of patterned gold nanoparticles deposited on silicon nanoporous pillar arrays", Applied Surface Science, vol. 257, No. 18, Apr. 25, 2011, p. 8089-p. 8092 XP028373693.

Su Yeon Lee, et al., "Freestanding and Arrayed Nanoporous Microcylinders for Highly Active 3D SERS Substrate", Chemistry of Materials, vol. 25, No. 12, Jun. 25, 2013, p. 2421-p. 2426, XP55286875.

W. Zhang et al., "Giant and uniform fluorescence enhancement over large areas using plamonic nanodots in 3D resonant cavity nanoantenna by nanoimprinting", Nanotechnology, vol. 23, No. 22, May 10, 2012, p. 225301, XP020224099.

S. M. Wells et al., "Efficient disc on pillar substrates for surface enhanced Raman spectroscopy", Chemical Communications—Chemcom, vol. 47, No. 13, Jan. 1, 2011, p. 3814-p. 3816, XP055289549.

Zhiqiang Sun et al., "Fabricating Ordered Microstructures on the Basis of Self-assembled Colloidal Crystals", Major: Polymer Chemistry and Physics, vol. 8, Aug. 15, 2009, p. B014-p. 158.

Zhida Xu et al., "Nanoreplicated positive and inverted submicrometer polymer pyramid array for surface-enhanced Raman spectroscopy," Journal of Nanophotonics, vol. 5, No. 1, Jan. 1, 2011, p. 053526, XP055284283.

Hiroshi Hiroshima et al., "Homogeneity of Residual Layer thickness in UV Nanoimprint Lithography," Japanese Journal of Applied Physics, Jun. 1, 2009, p. 6-p. 18, XP55284163.

Liu Gang et al., "Nanowell surface enhanced Raman scattering arrays fabricated by soft-lithography for label-free biomolecular detections in integrated microfluidics," Applied Physics Letters, vol. 87, No. 7, Aug. 11, 2005, p. 74101, XP012077510.

K. Nakamoto et al., "Arrays of Metallic Nanopillars in Holes for Plasmonic Devices", Retrieved from the Internet: URL: http://www.rsc.org/images/LOC/2011/PDFs/Papers/596_0021.pdf, Oct. 6, 2011, XP055289892.

M. Tomohiko et al., "New localized surface plasmon resonance sensor utilizing nanoimprinting technology", NSTI Nanotechnology Conference and Trade Show-NSTI Nanotech, vol. 1, May 11, 2006, p. 58-p. 61, XP009098538.

W. D. Li et al., "Three-dimensional cavity nanoantenna coupled plasmonic nanodots for ultrahigh and uniform surface-enhanced Raman scattering over large area", Optics Express, vol. 19, No. 5, Feb. 14, 2011, p. 3925-3936, XP002751299.

W. Wu et al., "Rational engineering of highly sensitive SERS substrate based on nanocone structures", Proceedings of SPIE, vol. 7673, Apr. 23, 2010, p. 767300-p. 767300-6, XP055172245.

U.S. Office Action dated Oct. 14, 2016 that issued in U.S. Appl. No. 14/420,510 including Double Patenting Rejections on pp. 2-14.

(56) References Cited

OTHER PUBLICATIONS

Di Zhi-gang et al., "Simulation and optimization of SERS effect in nano Ag substrates", Laser & Infrared, vol. 41, No. 8, Aug. 31, 2011, p. 850-p. 855.
U.S. Office Action dated Jun. 9, 2017 that issued in U.S. Appl. No. 14/780,776 including Double Patenting Rejections on pp. 8-10.

* cited by examiner

*Fig.6*
(a)
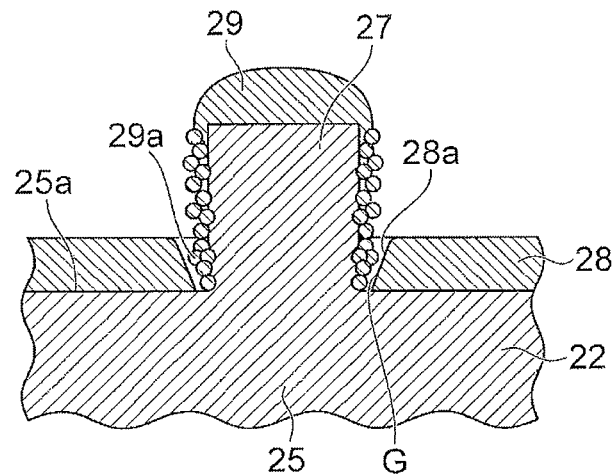
(b)
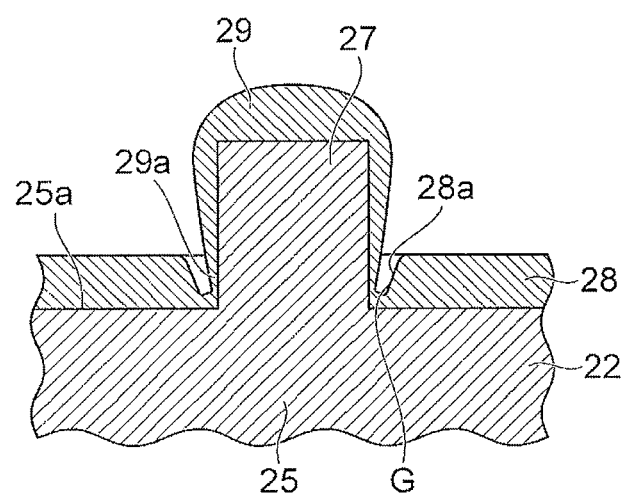
(c)
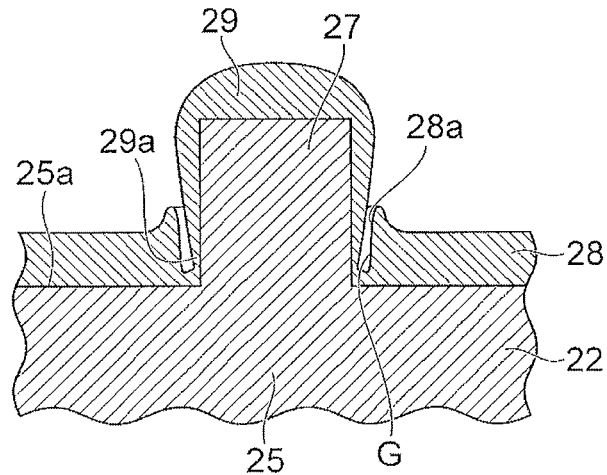

Fig.8
(a)
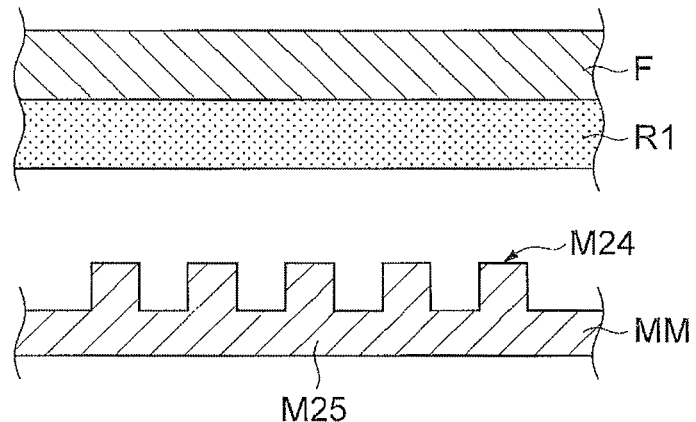
(b)
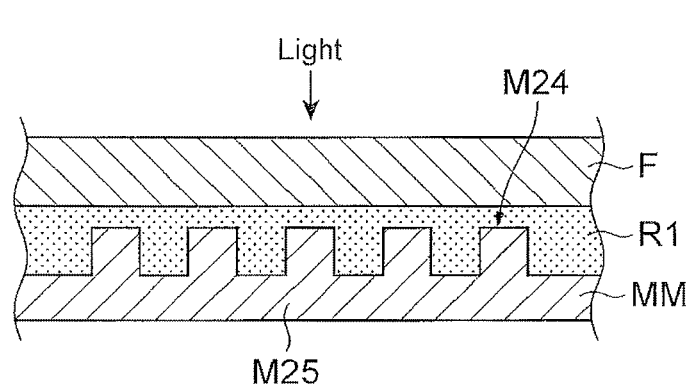
(c)
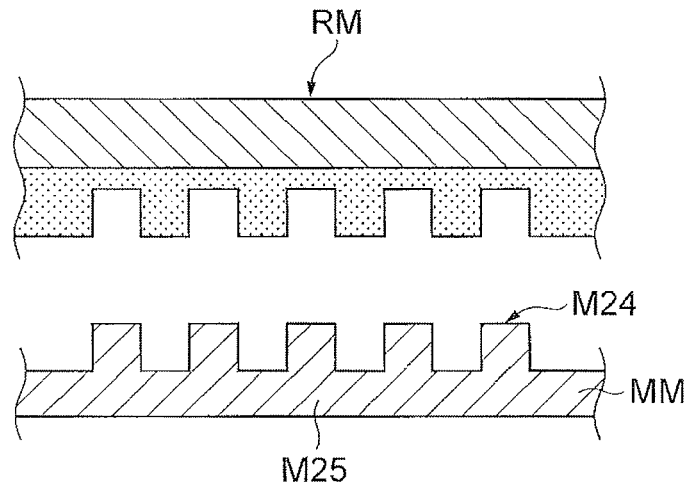

Fig.10
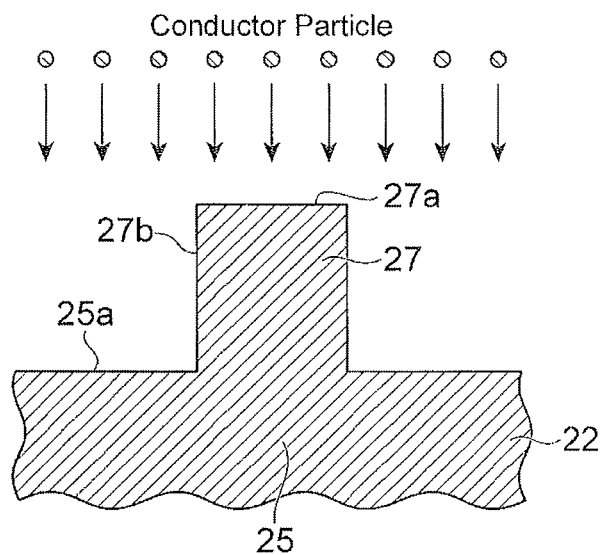
(a)
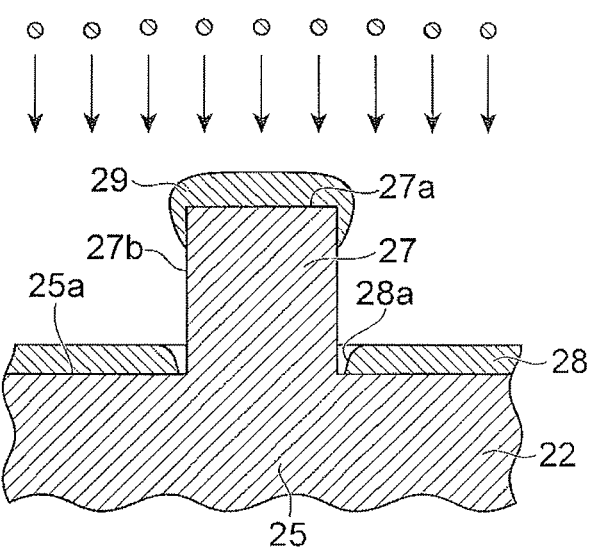
(b)
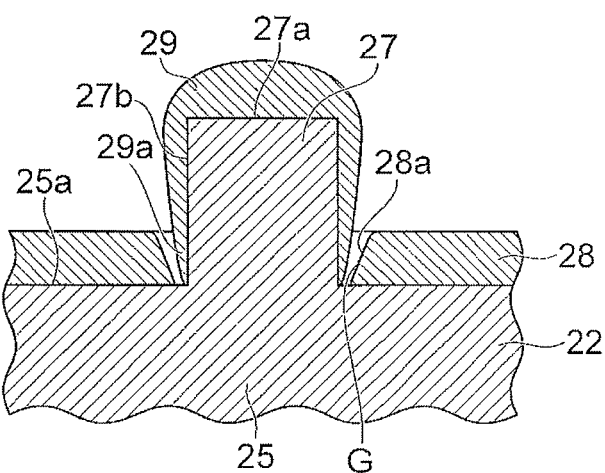
(c)

SURFACE-ENHANCED RAMAN SCATTERING ELEMENT

TECHNICAL FIELD

The present invention relates to a surface-enhanced Raman scattering element.

BACKGROUND ART

As a conventional surface-enhanced Raman scattering element, one equipped with a minute metal structure configured to generate surface-enhanced Raman scattering (SERS) has been known (see, for example, Patent Literature 1 and Non Patent Literature 1). In such a surface-enhanced Raman scattering element, when a sample to be subjected to Raman spectroscopic analysis is brought into contact with the minute metal structure and is irradiated with excitation light in this state, surface-enhanced Raman scattering occurs, whereby Raman scattering light enhanced by about $10^8$ times, for example, is released.

Meanwhile, for example, Patent Literature 2 discloses a minute metal structure in which metal layers are formed on one surface of a substrate and upper surfaces of a plurality of minute projections formed on the one surface of the substrate (or bottom faces of a plurality of fine holes formed on the one surface of the substrate) so as to be out of contact with each other (such that the shortest distance therebetween is on the order of 5 nm to 10 μm).

CITATION LIST

Patent Literature

Patent Literature 1: Japanese Patent Application Laid-Open No. 2011-33518
Patent Literature 2: Japanese Patent Application Laid-Open No. 2009-222507

Non Patent Literature

Non Patent Literature 1: "Q-SERS™ G1 Substrate", [online], Opto Science, Inc., [retrieved from the Internet on 2013 Jul. 5].

SUMMARY OF INVENTION

Technical Problem

When a minute metal structure is formed with a so-called nanogap as mentioned above, electric fields are locally enhanced upon irradiation with excitation light, whereby the intensity of surface-enhanced Raman scattering increases. For forming favorable nanogaps in the minute metal structure disclosed in Patent Literature 2, however, it is necessary to contrive the form of the minute projections.

It is therefore an object of the present invention to provide a surface-enhanced Raman scattering element which can increase the intensity of surface-enhanced Raman scattering by a favorable nanogap.

Solution to Problem

The surface-enhanced Raman scattering element in accordance with one aspect of the present invention comprises a substrate having a principal surface; a fine structure part formed on the principal surface and having a plurality of projections; and a conductor layer formed on the fine structure part and constituting an optical function part for generating surface-enhanced Raman scattering; the conductor layer having a base part formed along the principal surface and a plurality of protrusions protruding from the base part at respective positions corresponding to the projections; the base part being formed with a plurality of grooves surrounding the respective projections when seen in the projecting direction of the projections; a part of the protrusion being located within the groove corresponding thereto.

In this surface-enhanced Raman scattering element, a part of the protrusion in the conductor layer is located within the groove formed in the base part of the conductor layer so as to surround the projection of the fine structure part. As a consequence, a gap formed within the groove by the base part and protrusion favorably functions as a nanogap where electric fields are locally enhanced. Therefore, this surface-enhanced Raman scattering element can increase the intensity of surface-enhanced Raman scattering by favorable nanogaps.

In the surface-enhanced Raman scattering element in accordance with one aspect of the present invention, the projections may be arranged periodically along the principal surface. This configuration can stably increase the intensity of surface-enhanced Raman scattering.

In the surface-enhanced Raman scattering element in accordance with one aspect of the present invention, the grooves may extend like rings so as to surround the respective projections when seen in the projecting direction of the projections. This configuration can increase gaps which favorably function as nanogaps.

In the surface-enhanced Raman scattering element in accordance with one aspect of the present invention, the protrusion may have a form constricted at an end part on the substrate side. This configuration can securely position a part of the protrusion into the groove formed in the base part, thereby enabling the gap formed within the groove by the base part and protrusion to function favorably as a nanogap.

In the surface-enhanced Raman scattering element in accordance with one aspect of the present invention, a part of the protrusion located within the groove corresponding thereto may be in a state of agglomerated conductor particles. In the surface-enhanced Raman scattering element in accordance with one aspect of the present invention, the base part may bulge along an outer periphery of the groove. Each configuration can enable the gap formed within the groove by the base part and protrusion to function favorably as a nanogap.

In the surface-enhanced Raman scattering element in accordance with one aspect of the present invention, the base part and protrusion may be connected to each other at the deepest part of the groove. In the surface-enhanced Raman scattering element in accordance with one aspect of the present invention, the base part and protrusion may be separated from each other at the deepest part of the groove. Each configuration can enable the gap formed within the groove by the base part and protrusion to function favorably as a nanogap.

Advantageous Effects of Invention

The present invention can provide a surface-enhanced Raman scattering element which can increase the intensity of surface-enhanced Raman scattering by a favorable nanogap.

BRIEF DESCRIPTION OF DRAWINGS

FIG. 6 is a partly enlarged sectional view of a modified example of the surface-enhanced Raman scattering element in the surface-enhanced Raman scattering unit of FIG. 1;

FIG. 8 is a sectional view illustrating steps of manufacturing the surface-enhanced Raman scattering element of FIG. 5;

FIG. 10 is a sectional view illustrating steps of manufacturing the surface-enhanced Raman scattering element of FIG. 5;

DESCRIPTION OF EMBODIMENTS

Figure 1:
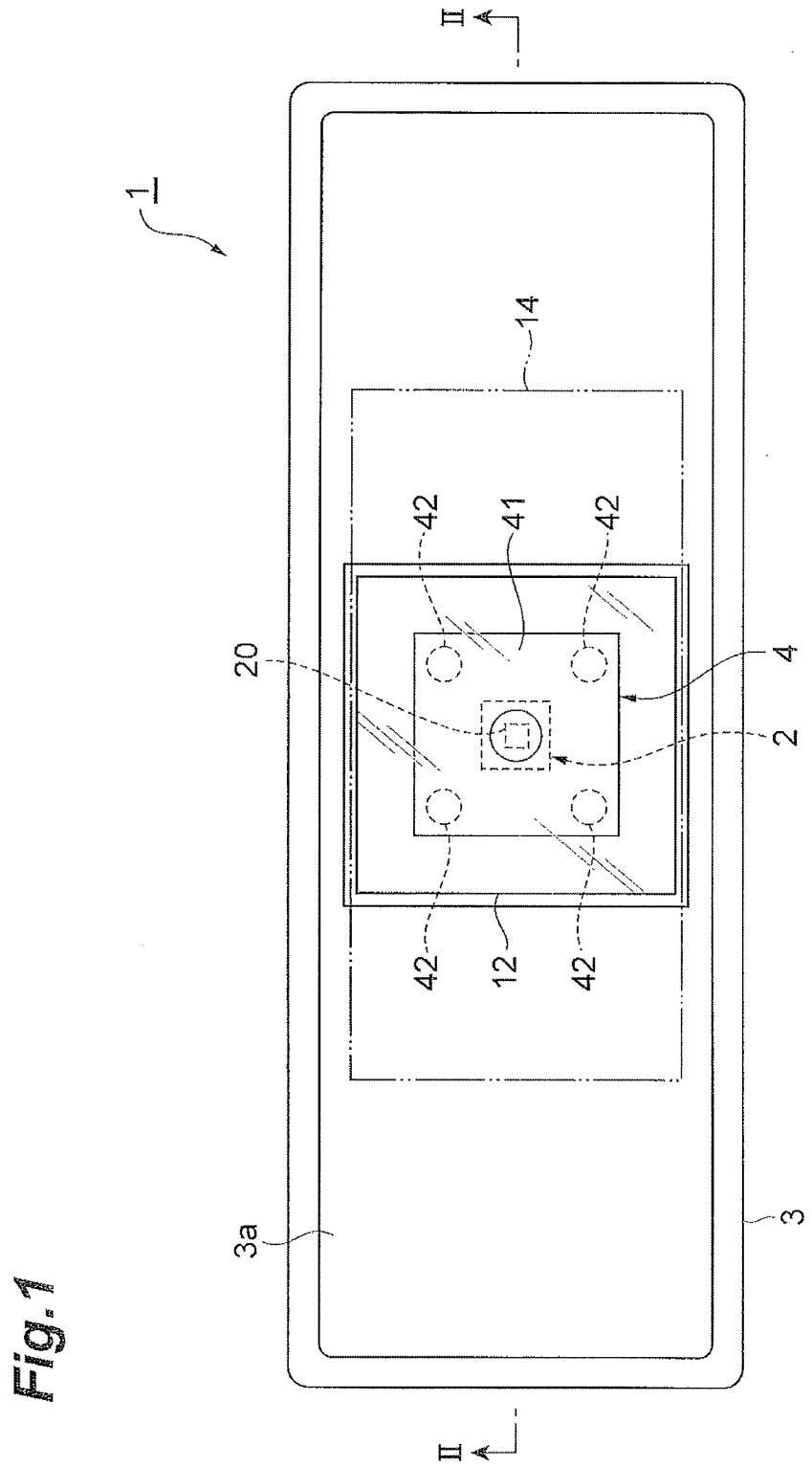
FIG. 1 is a plan view of a surface-enhanced Raman scattering unit employing a surface-enhanced Raman scattering element in accordance with an embodiment of the present invention.

In the following, preferred embodiments of the present invention will be explained in detail with reference to the drawings. In the drawings, the same or equivalent parts will be referred to with the same signs while omitting their overlapping descriptions.

Figure 2:
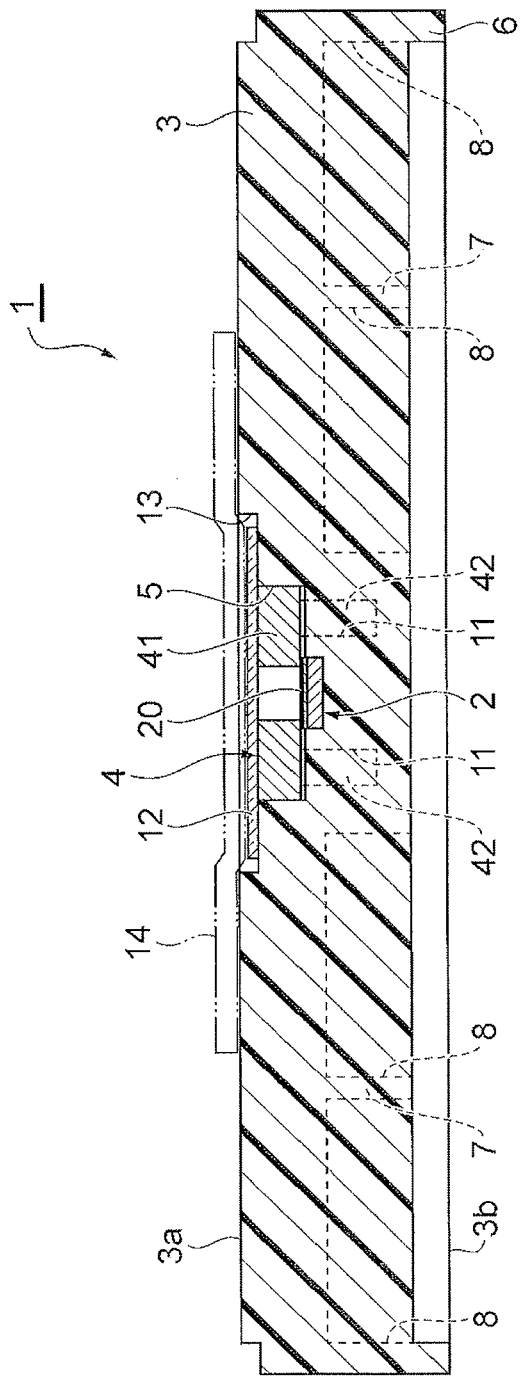
FIG. 2 is a sectional view of the surface-enhanced Raman scattering unit taken along the line II-II of FIG. 1.

As illustrated in FIGS. 1 and 2, a SERS unit (surface-enhanced Raman scattering unit) 1 comprises a SERS element (surface-enhanced Raman scattering element) 2, a measurement board 3 for supporting the SERS element 2 at the time of measurement, and a holding part 4 for mechanically holding the SERS element 2 in the measurement board 3. By "mechanically" is meant "by fitting between members without adhesives and the like."

Figure 3:
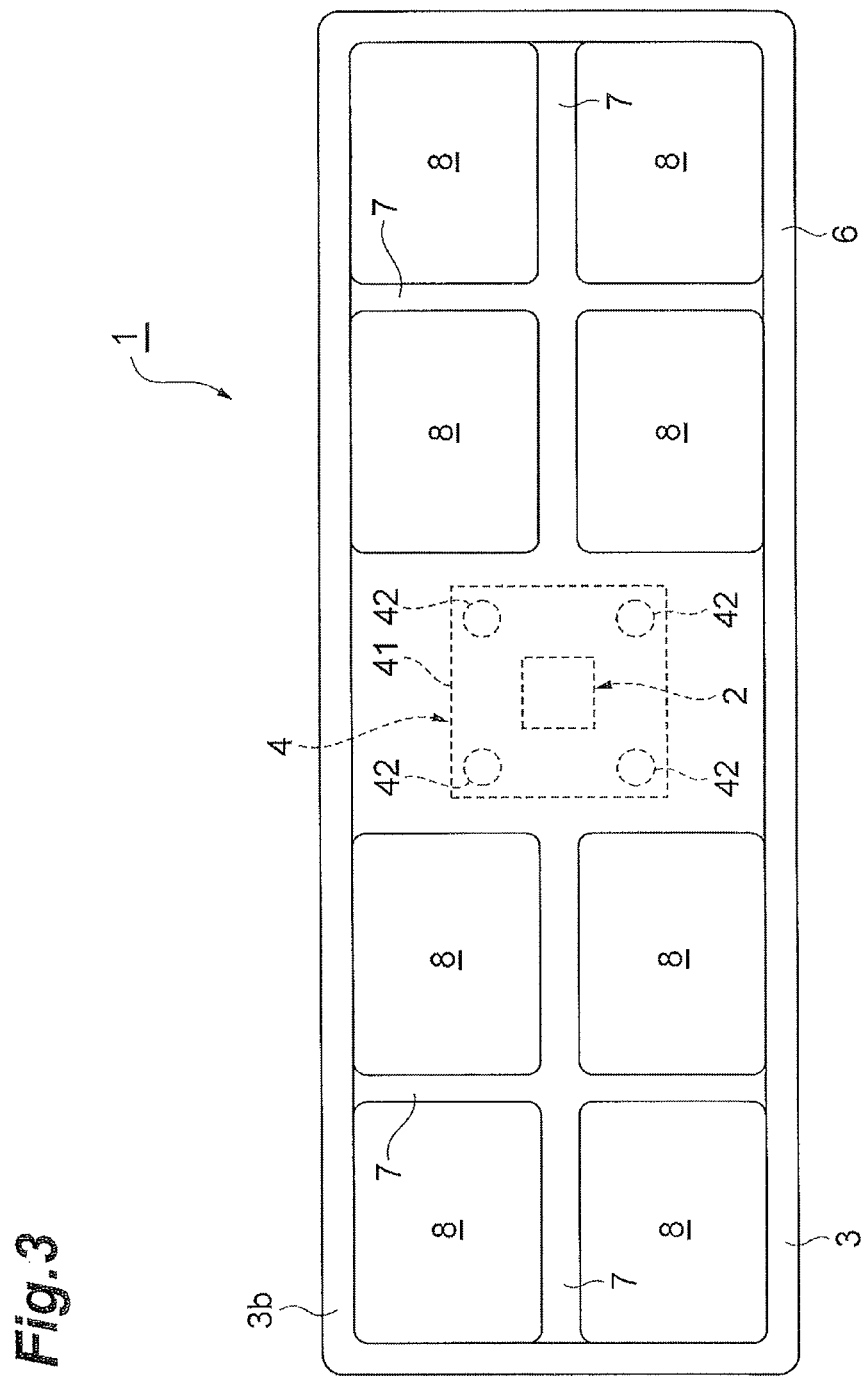
FIG. 3 is a bottom view of the surface-enhanced Raman scattering unit of FIG. 1.

The measurement board 3 has a front face 3a provided with a depression 5 for containing the SERS element 2 and holding part 4. On the other hand, as illustrated in FIGS. 2 and 3, the measurement board 3 has a rear face 3b provided with a plurality of hollowed parts 8 so as to form wall parts 6, 7 extending in directions perpendicular to the thickness direction of the measurement board 3. By way of example, the wall part 6 is formed like a ring along the outer edge of the measurement board 3, while the wall parts 7 are formed like a grid on the inside of the wall part 6. The measurement board 3 is formed into a rectangular plate. Each of the depression 5 and hollowed parts 8 is formed into a rectangular parallelepiped. The measurement board 3 like this is integrally formed from a material such as a resin (examples of which include polypropyrene, styrol resin, ABS resin, polyethylene, PET, PMMA, silicone, and liquid crystal polymers), ceramics, glass, or silicon by using a technique such as molding, cutting, or etching.

Figure 4:
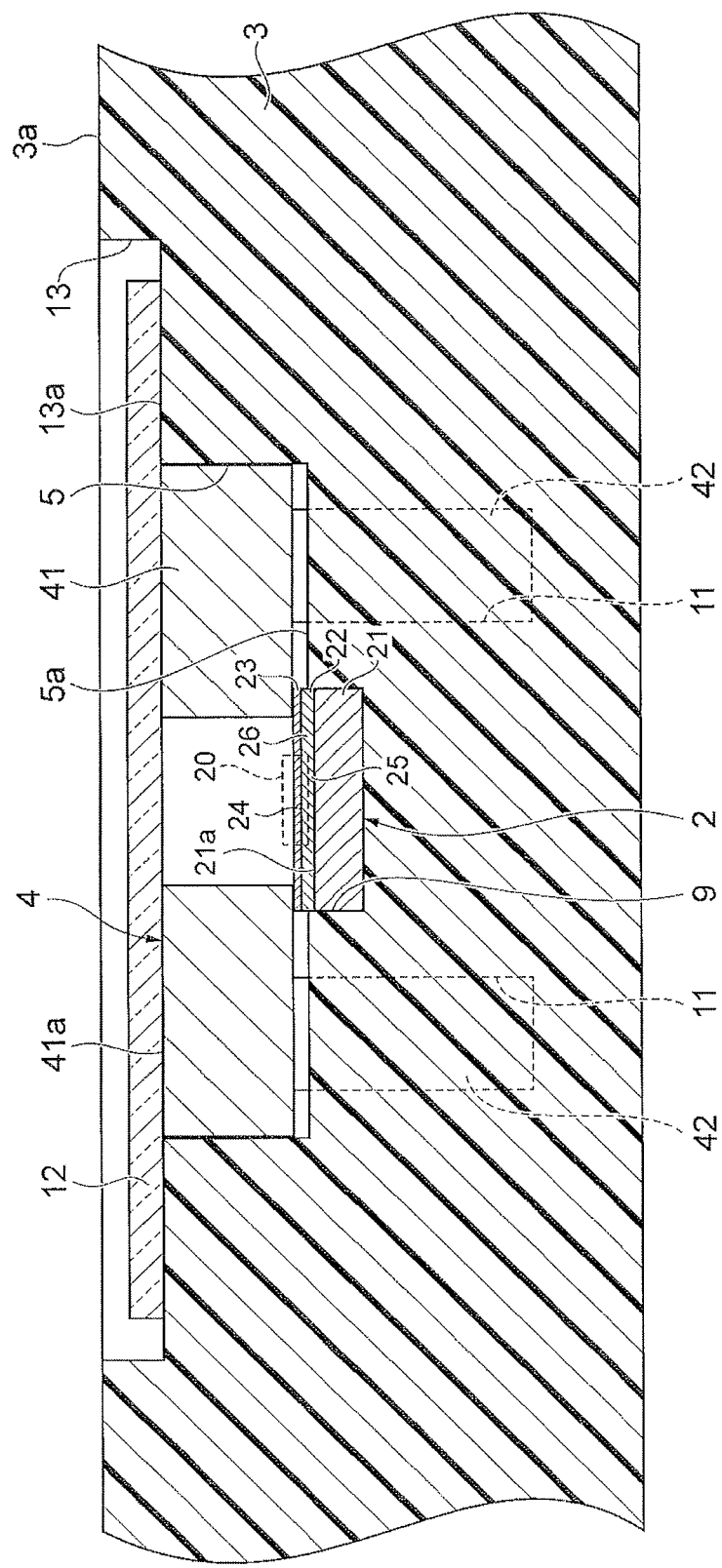
FIG. 4 is a partly enlarged sectional view of the surface-enhanced Raman scattering unit taken along the line II-II of FIG. 1.

As illustrated in FIG. 4, the SERS element 2 comprises a substrate 21, a. molded. layer 22 formed on the substrate 21, and a conductor layer 23 formed on the molded layer 22. By way of example, the substrate 21 is formed into a rectangular plate by silicon, glass, or the like and has an outer form on the order of several hundred μm×several hundred μm to several ten mm×several ten mm and a thickness on the order of 100 μm to 2 mm.

The molded layer 22 includes a fine structure part 24, a support part 25, and a frame part 26. The fine structure part 24, which is a region having a periodic pattern constructed on a surface layer on the side opposite from the substrate 21 at a center part of the molded layer 22, is formed on a front face (principal surface) 21a of the substrate 21 with the support part 25 interposed therebetween. The support part 25, which is a region supporting the fine structure part 24, is formed on the front face 21a of the substrate 21. The frame part 26, which is a ring-shaped region surrounding the support part 25, is formed on the front face 21a of the substrate 21.

By way of example, the fine structure part 24 has a rectangular outer form on the order of several hundred μm×several hundred μm to several ten mm×several ten mm when seen from one side in the thickness direction of the measurement board 3. In the fine structure part 24, as a periodic pattern, a plurality of pillars, each having a diameter and height on the order of several nm to several hundred nm, are periodically arranged at a pitch on the order of several ten nm to several hundred nm along the front face 21a of the substrate 21. The support part 25 and frame part 26 have a thickness on the order of several ten nm to several ten μm. The molded layer 22 like this is integrally formed by molding a resin (examples of which include resins based on acrylics, fluorine, epoxy, silicone, and urethane, PET, polycarbonate, and inorganic/organic hybrid materials) or low-melting glass arranged on the substrate 21 by nanoimprinting, for example.

The conductor layer 23 is integrally formed on the fine structure part 24 and frame part 26. In the fine structure part 24, the conductor layer 23 reaches a surface of the support part 25 which is exposed to the side opposite from the substrate 21. In the SERS element 2, the conductor layer 23 formed on the surface of the fine structure part 24 and on the surface of the support part 25 exposed to the side opposite from the substrate 21 constructs an optical function part 20 which generates surface-enhanced Raman scattering. By way of example, the conductor layer 23 has a thickness on the order of several nm to several μm. The conductor layer 23 like this is formed by vapor-depositing a conductor such as a metal (Au, Ag, Al, Cu, Pt, or the like) on the molded layer 22 molded by nanoimprinting, for example.

The depression 5 has a bottom face 5a provided with a recess 9 which contains a part on the substrate 21 side of the SERS element 2. The recess 9 is formed complementary to a part on the substrate 21 side of the SERS element 2 and restrains the SERS element 2 from moving in directions perpendicular to the thickness direction of the substrate 21.

The SERS element 2 is merely in contact with the inner surface of the recess 9 without being secured thereto with adhesives and the like. The recess 9 may contain substantially the whole SERS element 2 so that the front face (surface on the side opposite from the substrate 21) of the conductor layer 23 and the bottom face 5a of the depression 5 are substantially flush with each other.

The holding part 4 has a constraining part 41 formed like a ring so as to surround the optical function part 20 when seen in the thickness direction of the substrate 21 and a plurality of legs 42 extending from the constraining part 41 to the rear face 3b side of the measurement board 3. The bottom face 5a of the depression 5 is formed with fitting holes 11 corresponding to the respective legs 42. The legs 42 are fitted into the respective fitting holes 11 while the constraining part 41 surrounds the optical function part 20 and is in contact with the conductor layer 23 of the SERS element 2. Thus, the holding part 4 formed separately from the measurement board 3 is mechanically secured to the measurement board 3, while the SERS element 2 arranged in the recess 9 is held between the measurement board 3 and the constraining part 4 of the holding part 4. As a consequence, the SERS element 2 is mechanically held against the measurement board 3. The fitting holes 11 have bottoms and do not penetrate through the measurement board 3.

By way of example, the constraining part 41 is formed such as to have a rectangular outer edge and a circular inner edge when seen in the thickness direction of the substrate 21, while the legs 42 extend respectively from four corners of the constraining part 41 to the rear face 3b side of the measurement board 3. The constraining part 41 has the circular inner edge, thereby keeping pressures from locally acting on the SERS element 2. The legs 42 and fitting holes 11 are formed like cylinders. The holding part 4 having the constraining part 41 and legs 42 like these is integrally formed from a material such as a resin (examples of which include polypropyrene, styrol resin, ABS resin, polyethylene, PET, PMMA, silicone, and liquid crystal polymers), ceramics, glass, or silicon by using a technique such as molding, cutting, or etching.

The SERS unit 1 further comprises a light-transmitting cover 12. The cover 12 is arranged in a widened part 13 provided in the opening of the depression 5 and shields the opening of the depression 5. The widened part 13 is formed complementary to the cover 12 and restrains the cover 12 from moving in directions perpendicular to the thickness direction of the cover 12. The constraining part 41 of the holding part 4 has a surface 41a substantially flush with a bottom face 13a of the widened part 13. As a consequence, the cover 12 is supported not only by the measurement board 3 but also by the holding part 4. By way of example, the cover 12 is formed into a. rectangular plate by glass or the like and has an outer form on the order of 18 mm×18 mm and a thickness of about 0.15 mm. As illustrated in FIGS. 1 and 2, a temporary securing film 14 is attached to the SERS unit 1 before used so as to shield the cover 12, thereby preventing the cover 12 from dropping out of the measurement board 3.

Figure 5:
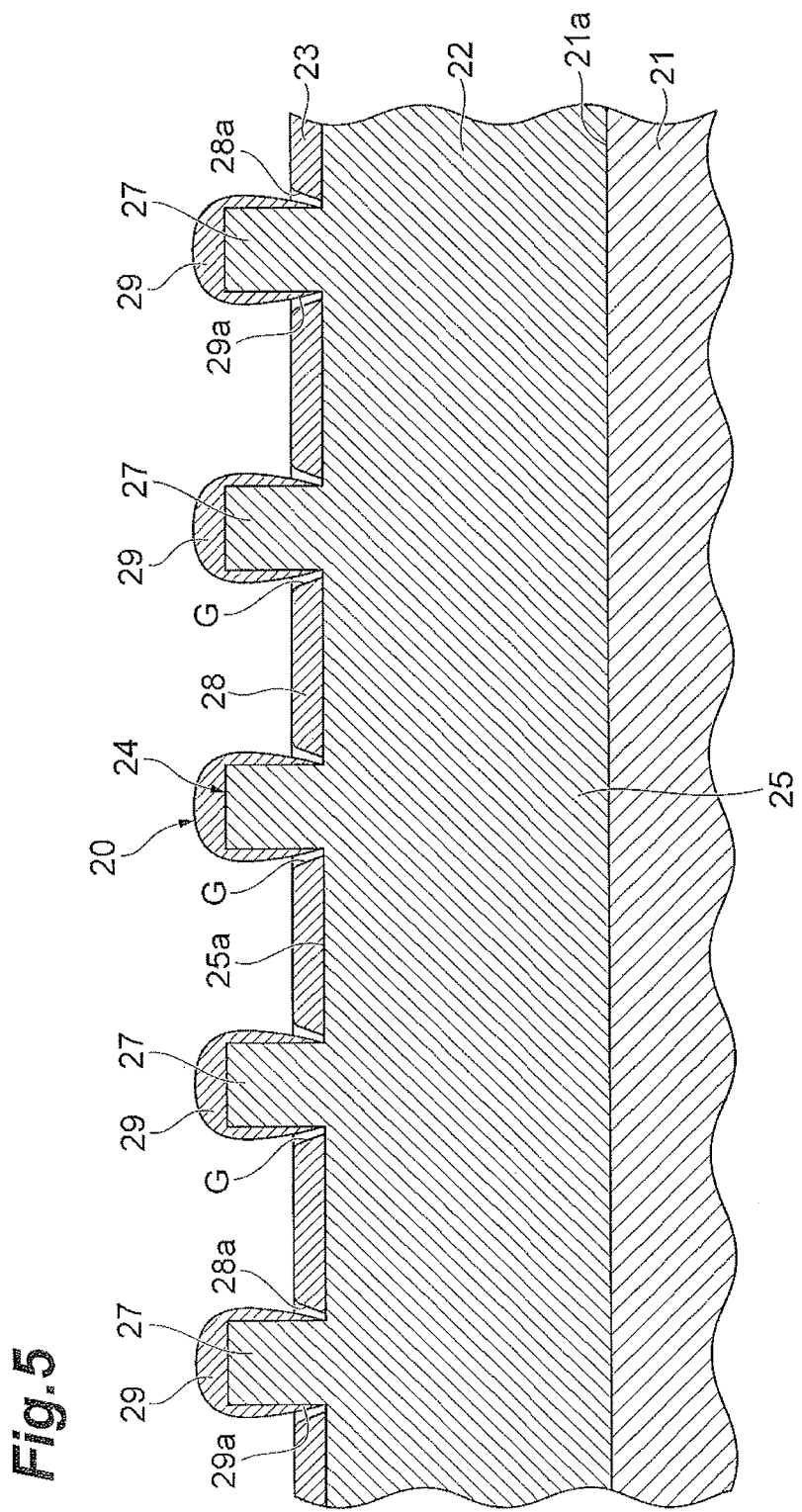
FIG. 5 is a partly enlarged sectional view of the surface-enhanced Raman scattering element in the surface-enhanced Raman scattering unit of FIG. 1.

The structure of the optical function part 20 in the above-mentioned SERS element 2 will be explained in more detail. As illustrated in FIG. 5, the fine structure part 24 has a plurality of pillars (projections) 27 periodically arranged along the front face 21a of the substrate 21. By way of example, the pillars 27, each of which is formed into a circular column having a diameter and height on the order of several nm to several hundred nm, are periodically arranged at a pitch on the order of several ten nm to several hundred nm (preferably 250 nm to 800 nm) along the front face 21a of the substrate 21.

The conductor layer 23 has a base part 28 formed along the front face 21a of the substrate 21 and a plurality of protrusions 29 protruding from the base part 28 at respective positions corresponding to the pillars 27. The base part 28 is formed like a layer on a surface 25a of the support part 25. The base part 28 has a thickness on the order of several nm to several hundred nm, which is smaller than the height of the pillars 27. Each protrusion 29 is produced so as to cover its corresponding pillar 27 and has a form constricted at least at an end part 29a on the substrate 21 side. In each protrusion 29, at least an end part on the side opposite from the substrate 21 (i.e., a part located on the top part of the pillar 27) protrudes from the base part 28.

The base part 28 is formed with a plurality of grooves 28a each opening to the side opposite from the substrate 21. Each groove 28a extends like a circular ring so as to surround its corresponding pillar 27 when seen in the projecting direction of the pillar 27 (i.e., the thickness direction of the substrate 21). The end part 29a on the substrate 21 side, which is a part of the protrusion 29, is located within its corresponding groove 28a (i.e., within the groove 28a surrounding the pillar 27 formed with the protrusion 29). As a consequence, within each groove 28a, the base part 28 and protrusion 29 form a gap G opening to the side opposite from the substrate 21. By way of example, the gap G is formed into a trench extending like a circular ring surrounding each pillar 27 when seen in the projecting direction of the pillar 27 and has a width on the order of 0 to several ten nm. While the outer side face defining the groove 28a is formed by the base part 28, the inner side face defining the groove 28a is not required to be the side face of the pillar but may be formed by the base part 28. The bottom face defining the groove 28a is not limited to the surface 25a of the support part 25 but may be formed by the base part 28.

As illustrated in (a) of FIG. 6, the end part 29a of the protrusion 29 located within its corresponding groove 28a may be in an agglomerated state (a state in which conductor particles are agglomerated). The base part 28 and protrusion 29 may be either connected to each other at the deepest part of the groove 28a as illustrated in (b) and (c) of FIG. 6 or separated from each other at the deepest part of the gap G as illustrated in FIG. 5 and (a) of FIG. 6. The base part 28 may bulge along the outer edge of the groove 28a as illustrated in (c) of FIG. 6.

Figure 7:
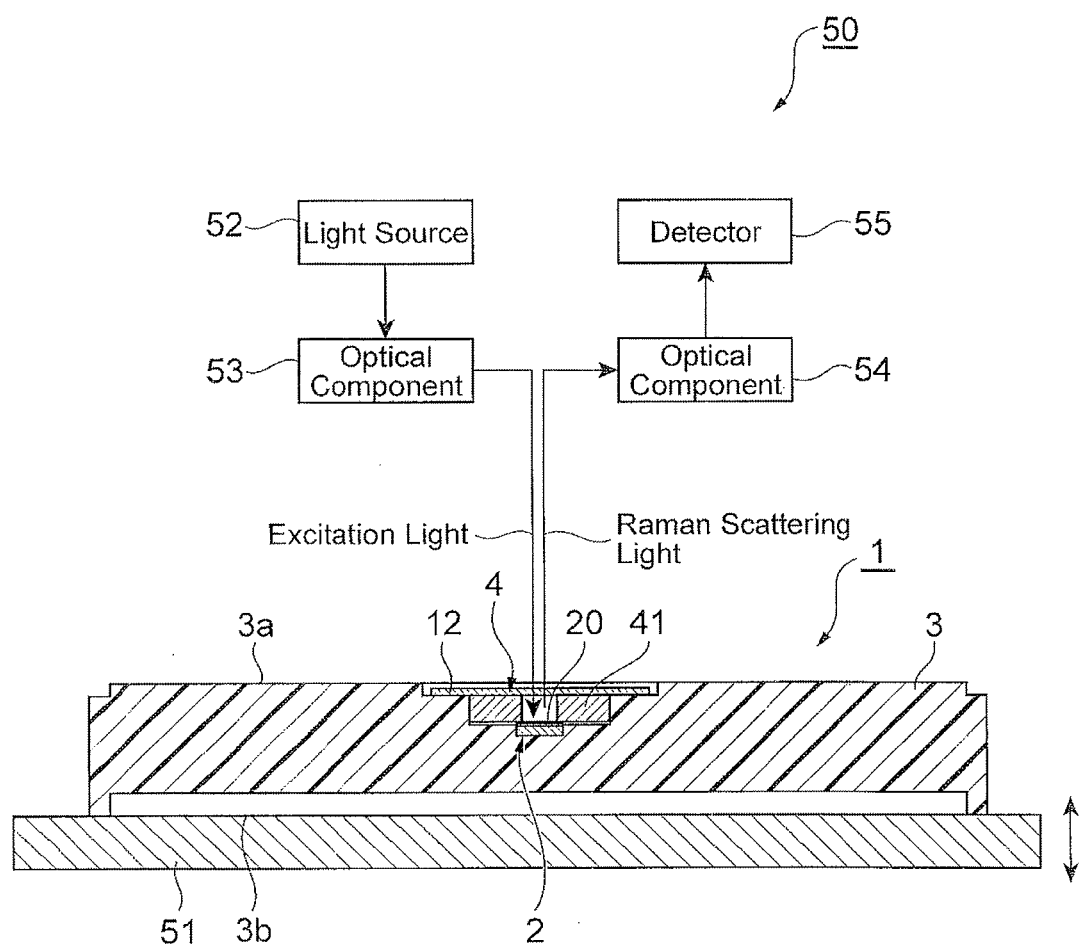
FIG. 7 is a structural diagram of a Raman spectroscopic analyzer in which the surface-enhanced Raman scattering unit of FIG. 1 is set.

A Raman spectroscopic analysis method by the SERS unit 1 constructed as in the foregoing will now be explained. Here, as illustrated in FIG. 7, the Raman spectroscopic analysis method is performed in a Raman spectroscopic analyzer 50 comprising a stage 51 for supporting the SERS unit 1, a light source 52 for emitting excitation light, an optical component 53 for carrying out collimation, filtering, condensing, and the like necessary for irradiating the optical function part 20 with the excitation light, an optical component 54 for carrying out collimation, filtering, and the like necessary for guiding Raman scattering light to a detector 55, and the detector 55 for detecting the Raman scattering light.

First, the SERS unit 1 is prepared, the temporary securing film 14 is peeled from the measurement board 3, and the cover 12 is removed from the measurement board 3. Then, a solution sample (or a dispersion of a powder sample in a solution such as water or ethanol) is dropped to a region on the inside of the constraining part 41 of the holding part 4, so as to arrange the solution sample on the optical function part 20. Subsequently, for reducing the lens effect, the cover 12 is arranged on the widened part 13 of the measurement board 3 and brought into close contact with the solution sample.

Thereafter, the measurement board 3 is arranged on the stage 51, and the SERS unit 1 is set in the Raman spectroscopic analyzer 50. Subsequently, the solution sample arranged on the optical function part 20 is irradiated with the excitation light emitted from the light source 52 through the optical component 53, so as to excite the solution sample. At this time, the stage 51 is moved such that the excitation light has a focal point located at the optical function part 20. This generates surface-enhanced Raman scattering at the interface between the optical function part 20 and solution sample, whereby surface-enhanced Raman scattering light derived from the solution sample is enhanced by about $10^8$ times, for example, and released. The released Raman scattering light is detected by the detector 55 through the optical component 54, whereby Raman spectroscopic analysis is performed.

Not only the above-mentioned method, but the following methods may also be used for arranging the sample on the optical function part 20. For example, while holding the measurement board 3, the SERS element 2 may be dipped in and lifted from the solution sample (or a dispersion of a powder sample in a solution such as water or ethanol), and then the sample may be blown to dry. A minute amount of the solution sample (or a dispersion of a powder sample in a solution such as water or ethanol) may be dropped onto the optical function part 20 and left to dry. A powder sample may be dispersed as it is on the optical function part 20. In these cases, it is not necessary for the cover 12 to be arranged at the time of measurement.

In the SERS element 2, as explained in the foregoing, the end part 29a of the protrusion 29 in the conductor layer 23 is located within the groove 28a formed in the base part 28 of the conductor layer 23 so as to surround the pillar 27 of the fine structure part 24. As a consequence, the gap G formed within the groove 28a by the base part 28 and protrusion 29 favorably functions as a nanogap where electric fields are locally enhanced. Therefore, the SERS element 2 can increase the intensity of surface-enhanced Raman scattering by favorable nanogaps.

In the SERS element 2, the pillars 27 are periodically arranged along the front face 21a of the substrate 21. This can increase the intensity of surface-enhanced Raman scattering.

In the SERS element 2, the groove 28a extends like a ring so as to surround each pillar 27 when seen in the projecting direction of the pillar 27. This can increase the gaps G favorably functioning as nanogaps.

In the SERS element 2, the protrusion 29 has a form constricted at the end part on the substrate 21 side. This can securely position the end part 29a of the protrusion 29 into the groove 28a formed in the base part 28, thereby enabling the gap G formed within the groove 28a by the base part 28 and protrusion 29 to function favorably as a nanogap.

Either when the end part 29a of the protrusion 29 located within the groove 28a is in the agglomerated state or the base part 28 bulges along the outer edge of the groove 28a, the gap G formed within the groove 28a by the base part 28 and protrusion 29 can favorably function as a nanogap. Similarly, the gap G formed within the groove 28a by the base part 28 and protrusion 29 can favorably function as a nanogap either when the base part 28 and protrusion 29 are connected to each other or separated from each other at the deepest part of the groove 28a.

A method for manufacturing the SERS element 2 will now be explained. First, as illustrated in (a) of FIG. 8, a film base F is prepared, and a UV-curable resin is applied to a surface of the film base F, so as to form a UV-curable resin layer R1 on the film base F. On the other hand, a master mold MM is prepared. The master mold MM includes a fine structure part M24 corresponding to the fine structure part 24 and a support part M25 for supporting the fine structure part M24. On the support part M25, a plurality of fine structure parts 24 are arranged in a matrix. The fine structure parts 24 are surface-treated with a releasing agent or the like so as to be released easily at a later step.

Next, as illustrated in (b) of FIG. 8, the master mold MM is pressed against the UV-curable resin layer R1 on the film base F, and the UV-curable resin R1 is irradiated with UV in this state, so as to be cured, whereby a pattern of the plurality of fine structure parts M24 are transferred to the UV-curable resin R1. Then, as illustrated in (c) of FIG. 8, the master mold MM is released from the UV-curable resin R1 on the film base F, so as to yield a replica mold (replica film) RM having the pattern of the plurality of fine structure parts M24 transferred thereto.

Figure 9:
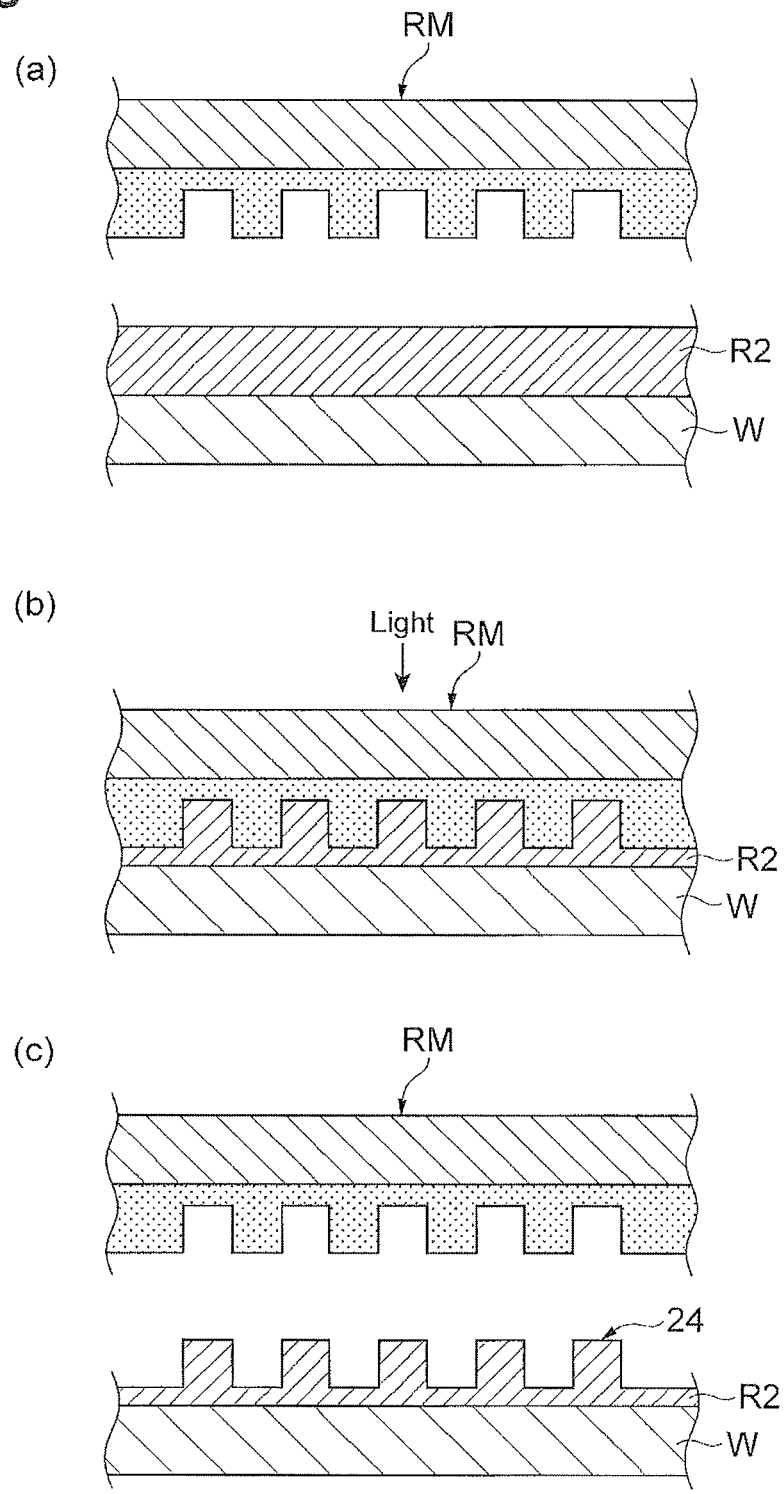
FIG. 9 is a sectional view illustrating steps of manufacturing the surface-enhanced Raman scattering element of FIG. 5.

Subsequently, as illustrated in (a) of FIG. 9, a silicon wafer W to become the substrate 21 is prepared, and a UV-curable resin is applied to a surface of the silicon wafer W, so as to form a nanoimprinting layer R2 to become the molded layer 22 on the silicon wafer W. Then, as illustrated in (b) of FIG. 9, the replica mold RM is pressed against the nanoimprinting layer R2 on the silicon wafer W, and the nanoimprinting layer R2 is irradiated with UV in this state, so as to be cured, whereby a pattern of the replica mold RM is transferred to the nanoimprinting layer. R2. Thereafter, as illustrated. in (c) of FIG. 9, the replica mold RM is released from the nanoimprinting layer R2 on the silicon wafer W, so as to yield the silicon wafer W formed with a plurality of fine structure parts 24.

The substrate 21 formed with the fine structure part 24 as in the foregoing is prepared on a wafer level, and a film of a metal such as Au or Ag is produced on the molded layer 22 by evaporation method, so as to form the conductor layer 23 constituting the optical function part 20 on the fine structure part 24. Subsequently, the silicon wafer W is cut for each fine structure part 24 (i.e., for each optical function part 20), whereby a plurality of SERS elements 2 are obtained. Here, the metal layer may be formed by vapor deposition after cutting the silicon wafer W into chips.

The fine structure part 24 may be formed on the substrate 21 by thermal nanoimprinting or etching using a mask having a two-dimensional pattern formed by photoetching, electron beam lithography, or the like instead of the above-mentioned nanoimprinting. For forming the conductor layer 23, a conductor layer such as a metal may be formed by vapor deposition methods (sputtering, CVD, and the like) other than the evaporation method.

As explained in the foregoing, the method for manufacturing the SERS element 2 can form the conductor layer 23 with the nano-order gaps G with a favorable reproducibility in a simple process, thereby enabling mass production of the SERS element 2.

Because of the following reason, producing the conductor layer 23 by using physical vapor deposition (PVD) such as evaporation method can favorably form the groove 28a in the base part 28 of the conductor layer 23 so as to surround the pillar 27 of the fine structure part 24 and favorably position the end part 29a of the protrusion 29 of the conductor layer 23 into the groove 28a. That is, atomized conductors (conductor particles) deposited on the fine structure part 24 from the projecting direction of the pillars 27 as illustrated in (a) of FIG. 10 are easier to reach (adhere to) the surface 25a of the support part 25 and the top part 27a of the pillar 27 as illustrated in (b) of FIG. 10. On the other hand, the conductor particles are harder to reach (adhere to) the root of the pillar 27 under a shadow effect of the conductor layer (protrusion 29) deposited on the top part 27a of the pillar 27. As a consequence, the groove 28a is formed in the base part 28 so as to surround the pillar 27. The conductor particles are also harder to adhere to a side face 27b of the pillar 27 under a similar shadow effect. This makes the protrusion 29 have a form constricted at the end part 29a, thereby positioning the end part 29a of the protrusion 29 into the groove 28a.

The following are sizes concerning the fine structure part 24 and base part 28 for favorably forming the grooves 28a in the base part 28 of the conductor layer 23 so as to surround the pillars 27 of the fine structure part 24 and positioning the end part 29a of the protrusion 29 of the conductor layer 23 into the groove 28a. Preferably, the pillars 27 have a diameter of 100 to 150 nm, a height of 120 to 200 nm, and a pillar pitch (distance between center lines of pillars adjacent to each other) of 300 to 450 nm. Preferably, the base part 28 has a thickness which is 20 to 60% of the height of the pillars 27.

Figure 11:
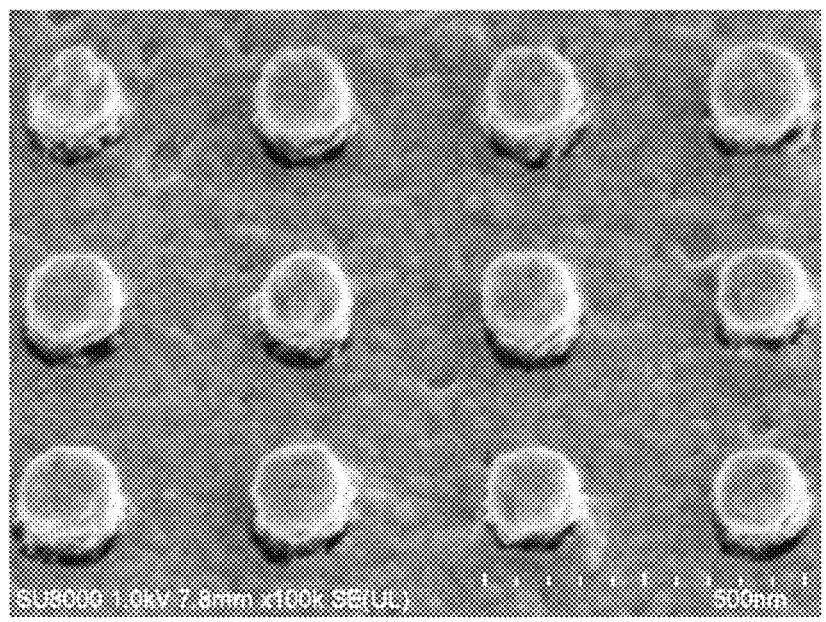
FIG. 11 is a SEM photograph of an optical function part in the surface-enhanced. Raman scattering element of Example 1.

Examples of the SERS element will now be explained. FIG. 11 is a SEM photograph of an optical function part in the SERS element of Example 1 (a SEM photograph capturing the optical function part in a direction tilted by 30° from a direction perpendicular to the surface of the substrate). In Example 1, Au is vapor-deposited as a conductor layer with a thickness of 50 nm. As illustrated in FIG. 11, it is seen in the SERS element of Example 1 that grooves are formed in the base part of the conductor layer so as to surround pillars of the fine structure part, that end parts of protrusions of the conductor layer are located within the grooves, and that a number of gaps favorably functioning as nanogaps are formed in the grooves.

The following is a specific method for making the SERS element of Example 1. First, using a mold in which holes, each having a hole diameter of 120 nm and a hole depth of 180 nm, were arranged in a square lattice at a hole interval (distance between center lines of holes adjacent to each other) of 360 nm, a resin on a substrate made of silicon was molded by nanoimprinting, so as to produce a fine structure part. In thus produced fine structure part, the pillars had a diameter of 120 nm, a height of 170 nm, and a pillar pitch (distance between center lines of pillars adjacent to each other) of 360 nm.

Next, a film of Au was formed as a conductor layer by resistance heating vacuum evaporation method on the produced fine structure part, so as to yield the SERS element of Example 1. The film forming condition for the conductor layer was "film thickness: as mentioned above; evaporation method rate: 0.1 nm/s; degree of vacuum during film forming: $1.5 \times 10^{-5}$ torr; substrate rotation: rotating dome at 5 rpm; substrate temperature control: none." For improving the adhesion of the conductor layer, a film of Ti may be formed as a buffer layer by resistance heating vacuum evaporation method on the produced fine structure part, and a film of Au may be formed as a conductor layer by resistance heating vacuum evaporation method on the buffer layer.

Figure 12:
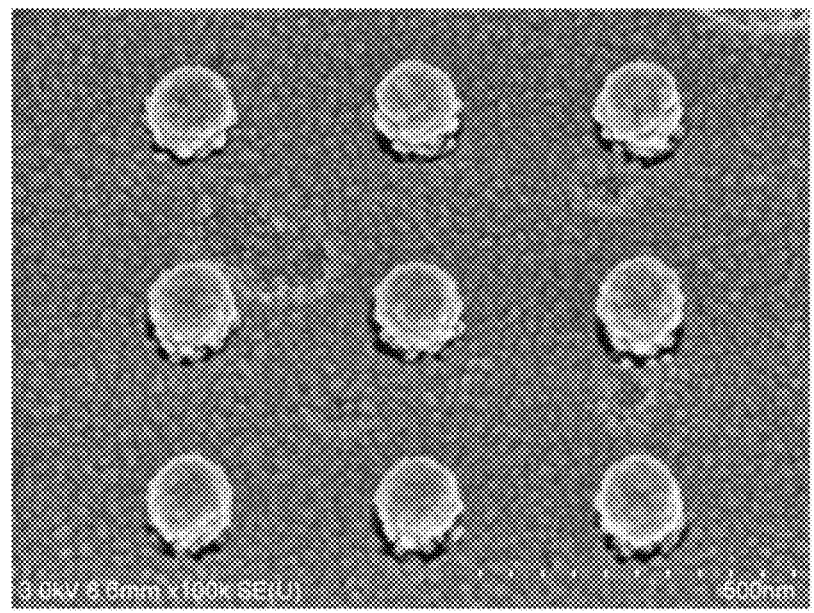
FIG. 12 is a SEM photograph of the optical function part in the surface-enhanced Raman scattering element of Example 2.

FIG. 12 is a SEM photograph of an optical function part in the SERS element of Example 2 (a SEM photograph capturing the optical function part in a direction tilted by 30° from a direction perpendicular to the surface of the substrate). In Example 2, Au is vapor-deposited as a conductor layer with a thickness of 50 nm. As illustrated in FIG. 12, it is also seen in the SERS element of Example 2 that grooves are formed in the base part of the conductor layer so as to surround pillars of the fine structure part, that end parts of protrusions of the conductor layer are located within the grooves, and that a number of gaps favorably functioning as nanogaps are formed in the grooves.

The following is a specific method for making the SERS element of Example 2. First, using a mold in which holes, each having a hole diameter of 120 nm and a hole depth of 180 nm, were arranged in a square lattice at a hole interval (distance between center lines of holes adjacent to each other) of 360 nm, a resin on a substrate made of glass was molded by nanoimprinting, so as to produce a fine structure part. In thus produced fine structure part, the pillars had a diameter of 120 nm, a height of 150 inn, and a pillar pitch (distance between center lines of pillars adjacent to each other) of 360 nm.

Next, a film of Au was formed as a conductor layer by resistance heating vacuum evaporation method on the produced fine structure part, so as to yield the SERS element of Example 2. The film forming condition for the conductor layer was "film thickness: as mentioned above; evaporation method rate: 0.02 m/s; degree of vacuum during film forming: $1.5 \times 10^{-5}$ torr; substrate rotation: none; substrate temperature control: none." For improving the adhesion of the conductor layer, a film of Ti may be formed as a buffer layer by resistance heating vacuum evaporation method on the produced fine structure part, and a film of Au may be formed as a conductor layer by resistance heating vacuum evaporation method on the buffer layer.

Figure 13:
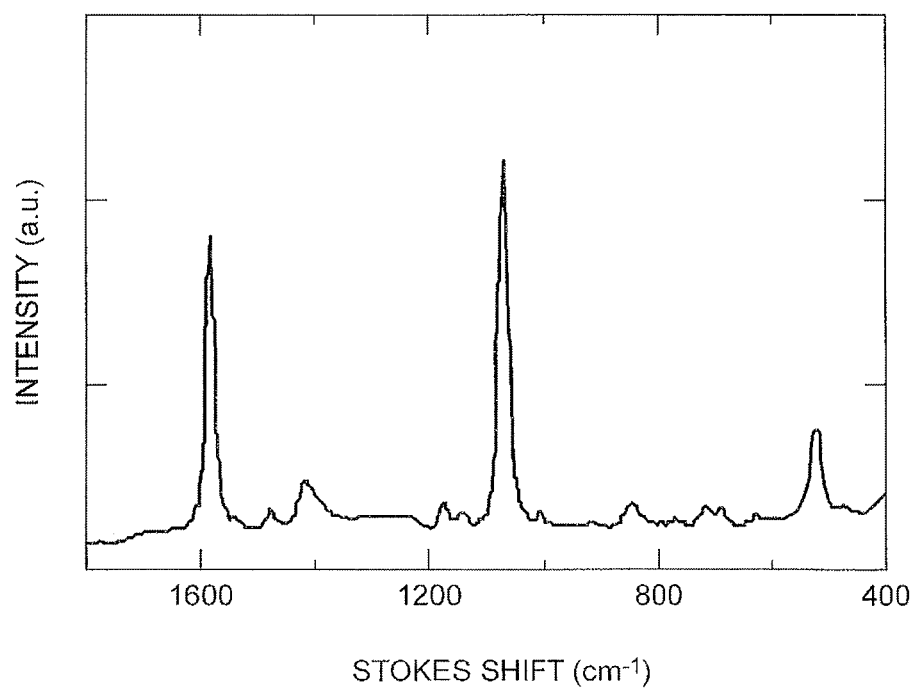
FIG. 13 is a graph illustrating a relationship between Stokes shift and signal intensity concerning the surface-enhanced Raman scattering element of Example 2.
Figure 14:
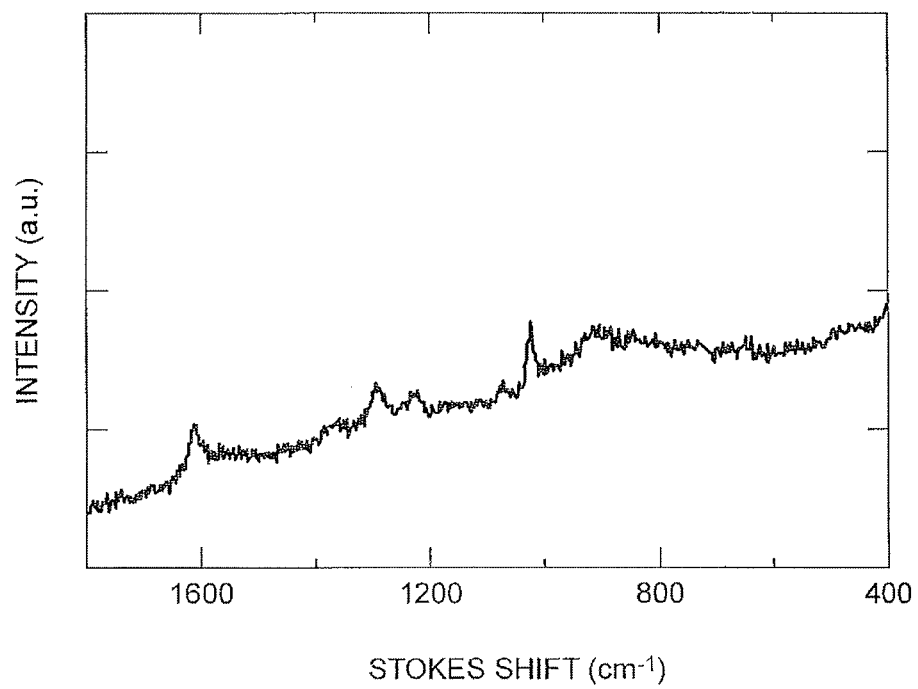
FIG. 14 is a graph illustrating a relationship between Stokes shift and signal intensity concerning the surface-enhanced Raman scattering element of Example 2.

FIGS. 13 and 14 are graphs illustrating relationships between Stokes shift and signal intensity concerning the surface-enhanced Raman scattering element of Example 2. FIG. 13 illustrates results obtained when Raman spectrometry was performed as follows. That is, the SERS element of Example 2 was dipped in an ethanol solution of mercaptobenzonic acid (1 mM) for two hours, rinsed with ethanol, and dried in a nitrogen gas, and then a sample was arranged on the optical function part of the SERS element. The sample was subjected to Raman spectrometry with excitation light having a wavelength of 785 nm. This resulted in a SERS spectrum of mercaptobenzonic acid as illustrated in FIG. 13. FIG. 14 illustrates results obtained when Raman spectrometry was performed as follows. That is, an aqueous solution of 4,4'-bipyridyl (0.1 μM) was dropped onto the optical function part of the SERS element of Example 2, and a glass cover was put thereon so as to prevent it from drying, whereby the sample was arranged on the optical function part. The sample was subjected to Raman spectrometry with excitation light having a wavelength of 785 nm. This resulted in a SERS spectrum of 4,4'-bipyridyl as illustrated in FIG. 14.

While an embodiment of the present invention is explained in the foregoing, the present invention is not limited to the above-mentioned embodiment. For example, the arrangement structure of the pillars 27 may be one dimensional instead of two dimensional, a triangle lattice instead of a square lattice, or non-periodic. The cross-sectional form of the pillars 27 is not limited to circles, but may be ellipses or polygons such as triangles and quadrangles. The groove 28a may also be formed so as to surround the pillar 27 in ring forms (such as ellipses) other than circles. The groove 28a may not be formed so as to surround the pillar 27 continuously but intermittently in a state divided into a plurality of regions. Thus, without being restricted to those mentioned above, various materials and forms can be employed for constituents of the SERS element 2.

When attention is focused on a pair of projections (those corresponding to the pillars 27) adjacent to each other, the width of the gap formed by the base part and protrusion is smaller than the distance between the conductor layer formed on the outer surface of one projection and that formed on the outer surface of the other projection. This can easily and stably form such a narrow gap (gap favorably functioning as a nanogap) as to be unattainable by the configuration of the fine structure part alone.

The fine structure part 24 may be formed on the front face 21*a* of the substrate 21 either indirectly with the support part 25, for example, interposed therebetween as in the above-mentioned embodiment or directly. The conductor layer 23 may be formed on the fine structure part 24 either indirectly with a layer such as a buffer metal (Ti, Cr, or the like) for improving the adhesion of a metal to the fine structure part 24, for example, interposed therebetween or directly.

INDUSTRIAL APPLICABILITY

The present invention can provide a surface-enhanced Raman scattering element which can increase the intensity of surface-enhanced Raman scattering by a favorable nanogap.

REFERENCE SIGNS LIST

2: SERS element (surface-enhanced Raman scattering element); 20: optical function part; 21: substrate; 21*a*: front face (principal surface); 23: conductor layer; 24: fine structure part; 27: pillar (projection); 28: base part; 28*a*: groove; 29: protrusion; 29*a*: end part (a part); G: gap.

The invention claimed is:

1. A surface enhanced Raman scattering element comprising:
    a substrate having a principal surface;
    a fine structure part formed on the principal surface and having a plurality of projections; and
    a conductor layer formed on the fine structure part and constituting an optical function part for generating surface-enhanced Raman scattering;
    wherein the conductor layer has a base part formed along the principal surface and a plurality of protrusions protruding from the base part at respective positions corresponding to the projections;
    wherein the base part is formed with a plurality of grooves surrounding the respective projections when seen in a projecting direction of the projections;
    wherein a part of the protrusion is located within the groove corresponding thereto; and
    wherein the groove has a depth in the projecting direction of the projections equal to or smaller than a thickness of the base part,
    each projection is a pillar, and
    the groove is formed in a region surrounding the pillar, the region is located at a substrate side relative to an edge of a side face of the base part situated away from the substrate in the direction in which the pillar projects.

2. A surface-enhanced Raman scattering element according to claim 1, wherein the projections are arranged periodically along the principal surface.

3. A surface-enhanced Raman scattering element according to claim 1, wherein the grooves extend like rings so as to surround the respective projections when seen in the projecting direction of the projections.

4. A surface-enhanced Raman scattering element according to claim 1, wherein the protrusion has a form constricted at an end part on the substrate side.

5. A surface-enhanced Raman scattering element according to claim 1, wherein a part of the protrusion located within the groove corresponding thereto is in a state of agglomerated conductor particles.

6. A surface-enhanced Raman scattering element according to claim 1, wherein the base part bulges along an outer periphery of the groove.

7. A surface-enhanced Raman scattering element according to claim 1, wherein the base part and the protrusion are connected to each other at the deepest part of the groove.

8. A surface-enhanced Raman scattering element according to claim 1, wherein the base part and the protrusion are separated from each other at the deepest part of the groove.

* * * * *